(12) United States Patent
Takahashi et al.

(10) Patent No.: US 7,877,129 B2
(45) Date of Patent: Jan. 25, 2011

(54) MAGNETIC RESONANCE IMAGING APPARATUS AND RF RECEPTION COIL APPARATUS

(75) Inventors: Tetsuhiko Takahashi, Saitama (JP); Masahiro Takizawa, Chiba (JP)

(73) Assignee: Hitachi Medical Corporation (JP)

( * ) Notice: Subject to any disclaimer, the term of this patent is extended or adjusted under 35 U.S.C. 154(b) by 1040 days.

(21) Appl. No.: 10/489,069

(22) PCT Filed: Sep. 13, 2002

(86) PCT No.: PCT/JP02/09392

§ 371 (c)(1),
(2), (4) Date: Sep. 20, 2004

(87) PCT Pub. No.: WO03/024327

PCT Pub. Date: Mar. 27, 2003

(65) Prior Publication Data

US 2005/0033150 A1    Feb. 10, 2005

(30) Foreign Application Priority Data

Sep. 13, 2001    (JP) .............................. 2001-277891

(51) Int. Cl.
*A61B 5/00*    (2006.01)
(52) U.S. Cl. ..................... 600/410; 600/422; 324/307; 324/318
(58) Field of Classification Search ......... 324/307–309, 324/318; 600/410–415, 417, 422
See application file for complete search history.

(56) References Cited

U.S. PATENT DOCUMENTS 4,452,863 A    6/1984    Takizawa et al.
4,749,501 A    6/1988    Nakagawa
4,777,089 A    10/1988    Takizawa et al.
4,982,096 A    1/1991    Fujii et al.

(Continued)

FOREIGN PATENT DOCUMENTS

GB    2266775 A    11/1993

(Continued)

OTHER PUBLICATIONS

Jun. 9, 2009 Japanese official action in connection with a counterpart Japanese patent application No. 2001-277891.

(Continued)

*Primary Examiner*—Brian Casler
*Assistant Examiner*—Amanda Lauritzen
(74) *Attorney, Agent, or Firm*—Cooper & Dunham LLP

(57) ABSTRACT

An RF receiving means, which comprise respective at least three RF receiving coils (203, 201 (or 202), 204), (205, 202 (or 201), 206), (207, 201 (or 202), 208) disposed in at least two orthogonal directions (x, y, z), are set to a patient 209, any one direction (x) of the two directions is set as a phase encoding direction, magnetic resonance signals are measured by executing a pulse sequence while thinning phase encoding steps, and the aliasing of an image is eliminated by an arithmetic operation executed using the magnetic resonance signals measured by at least the three RF receiving coils (205, 202 (or 201), 206) disposed in the thus set phase encoding direction and using the sensitivity distributions of the respective RF receiving coils.

10 Claims, 7 Drawing Sheets

U.S. PATENT DOCUMENTS

| | | | |
|---|---|---|---|
| 5,103,092 A | 4/1992 | Takahashi et al. | |
| 5,164,973 A | 11/1992 | Takahashi et al. | |
| 5,280,246 A | 1/1994 | Takahashi et al. | |
| 5,453,692 A | 9/1995 | Takahashi et al. | |
| 5,457,386 A | 10/1995 | Matsunaga et al. | |
| 5,477,145 A | 12/1995 | Takahashi et al. | |
| 5,489,847 A | 2/1996 | Nabeshima et al. | |
| 5,544,653 A | 8/1996 | Takahashi et al. | |
| 5,552,707 A | 9/1996 | Takahashi et al. | |
| 5,592,088 A | 1/1997 | Matsunaga et al. | |
| 5,653,233 A * | 8/1997 | Pelc et al. | 600/410 |
| 5,755,665 A | 5/1998 | Takahashi et al. | |
| 5,928,146 A | 7/1999 | Itagaki et al. | |
| 5,951,474 A | 9/1999 | Matsunaga et al. | |
| 6,073,043 A * | 6/2000 | Schneider | 600/424 |
| 6,118,273 A | 9/2000 | Takizawa et al. | |
| 6,169,398 B1 | 1/2001 | Watanabe et al. | |
| 6,289,232 B1 * | 9/2001 | Jakob et al. | 600/410 |
| 6,326,786 B1 * | 12/2001 | Pruessmann et al. | 324/312 |
| 6,366,091 B1 | 4/2002 | Takahashi et al. | |
| 6,366,092 B1 * | 4/2002 | Ehnholm et al. | 324/309 |
| 6,396,269 B1 * | 5/2002 | Hajnal et al. | 324/309 |
| 6,448,771 B1 * | 9/2002 | Harvey et al. | 324/307 |
| 6,483,308 B1 * | 11/2002 | Ma et al. | 324/312 |
| 6,492,814 B1 * | 12/2002 | Watkins et al. | 324/318 |
| 6,493,572 B1 * | 12/2002 | Su et al. | 600/422 |
| 6,541,970 B1 | 4/2003 | Takizawa et al. | |
| 6,559,642 B2 * | 5/2003 | King | 324/307 |
| 6,566,878 B1 | 5/2003 | Komura et al. | |
| 6,615,069 B1 | 9/2003 | Komura et al. | |
| 6,653,834 B2 * | 11/2003 | Beck et al. | 324/309 |
| 6,728,568 B1 | 4/2004 | Yatsui et al. | |
| 6,777,934 B2 | 8/2004 | Takahashi et al. | |
| 6,833,700 B2 * | 12/2004 | Lee et al. | 324/307 |
| 6,876,198 B2 | 4/2005 | Watanabe et al. | |
| 6,876,201 B2 | 4/2005 | Takizawa | |
| 6,885,885 B1 | 4/2005 | Takizawa et al. | |
| 6,900,635 B1 * | 5/2005 | Petropoulos et al. | 324/318 |
| 6,906,515 B2 | 6/2005 | Yatsui et al. | |
| 6,930,480 B1 * | 8/2005 | Fujita et al. | 324/318 |
| 6,930,481 B2 * | 8/2005 | Okamoto et al. | 324/318 |
| 6,965,232 B2 * | 11/2005 | Sodickson | 324/307 |
| 6,975,115 B1 * | 12/2005 | Fujita et al. | 324/318 |
| 7,019,523 B2 * | 3/2006 | Ikezaki | 324/309 |
| 7,026,818 B2 * | 4/2006 | Machida et al. | 324/322 |
| 7,061,242 B2 | 6/2006 | Ochi et al. | |
| 7,196,518 B2 | 3/2007 | Yatsui et al. | |
| 7,205,765 B2 * | 4/2007 | Machida et al. | 324/318 |
| 7,221,161 B2 * | 5/2007 | Fujita et al. | 324/318 |
| 7,372,269 B2 * | 5/2008 | Takizawa et al. | 324/309 |
| 7,375,524 B2 * | 5/2008 | Katscher et al. | 324/309 |
| 2002/0013526 A1 * | 1/2002 | Su et al. | 600/422 |
| 2004/0015071 A1 | 1/2004 | Komura et al. | |
| 2004/0056660 A1 | 3/2004 | Yatsui et al. | |
| 2004/0061498 A1 | 4/2004 | Ochi et al. | |
| 2004/0092813 A1 | 5/2004 | Takizawa et al. | |
| 2004/0135579 A1 | 7/2004 | Takizawa et al. | |
| 2004/0189299 A1 * | 9/2004 | Ikezaki | 324/309 |
| 2005/0033152 A1 * | 2/2005 | Sinnema et al. | 600/410 |
| 2005/0070784 A1 | 3/2005 | Komura et al. | |
| 2006/0049829 A1 | 3/2006 | Takizawa et al. | |
| 2006/0058629 A1 * | 3/2006 | Warntjes et al. | 600/410 |
| 2006/0091884 A1 | 5/2006 | Takahashi et al. | |
| 2006/0125475 A1 * | 6/2006 | Sodickson et al. | 324/300 |
| 2006/0181279 A1 * | 8/2006 | Okamoto et al. | 324/318 |
| 2006/0183996 A1 | 8/2006 | Abe et al. | |
| 2006/0232273 A1 | 10/2006 | Takizawa et al. | |
| 2006/0255802 A1 | 11/2006 | Hirata et al. | |
| 2007/0078333 A1 | 4/2007 | Abe et al. | |
| 2007/0229075 A1 * | 10/2007 | Ookawa et al. | 324/318 |

FOREIGN PATENT DOCUMENTS

| | | |
|---|---|---|
| JP | 10-179545 | 7/1998 |
| JP | 10-248823 | 9/1998 |
| JP | 11-56811 | 3/1999 |
| JP | 11-113877 | 4/1999 |
| JP | 11-113878 | 4/1999 |
| JP | 2000-41970 | 2/2000 |
| JP | 2000-157507 | 6/2000 |
| JP | 2000-287949 | 10/2000 |
| JP | 2001-95775 | 4/2001 |
| JP | 2001-112735 | 4/2001 |
| JP | 2001-161657 | 6/2001 |
| JP | 2001-292976 | 10/2001 |
| JP | 2001-340316 | 12/2001 |
| JP | 2002-85376 | 3/2002 |
| JP | 2002-248089 | 9/2002 |
| JP | 2002-253524 | 9/2002 |
| JP | 2002-272700 | 9/2002 |
| JP | 2002-315731 | 10/2002 |
| JP | 2003-52664 | 2/2003 |
| JP | 2003-52665 | 2/2003 |
| JP | 2003-79595 | 3/2003 |
| JP | 2003-325469 | 11/2003 |
| JP | 2003-325473 | 11/2003 |
| JP | 2004-89275 | 3/2004 |
| JP | 2004-229865 | 8/2004 |
| JP | 2004-344183 | 12/2004 |
| JP | 2005-80855 | 3/2005 |
| JP | 2005-111059 | 4/2005 |
| JP | 2005-211187 | 8/2005 |
| JP | 2005-319074 | 11/2005 |
| JP | 2006-25845 | 2/2006 |
| JP | 2006-26076 | 2/2006 |
| JP | 2006-231076 | 9/2006 |
| JP | 2006-314491 | 11/2006 |
| JP | 2007-14813 | 1/2007 |
| JP | 2007-50278 | 3/2007 |
| WO | WO00/72752 A1 | 12/2000 |
| WO | WO03/092497 A1 | 11/2003 |
| WO | WO2004/060156 A1 | 7/2004 |
| WO | WO2004/080301 A1 | 9/2004 |

OTHER PUBLICATIONS

Aug. 25, 2009 Japanese official action in connection with a counterpart Japanese patent application No. 2001-277891.

Stensgaard, A., "A Four-Mode Shielded Loop Coil-System," *Proceedings of the International Society for Magnetic Resonance in Medicine*, vol. 1998, Issue S1, #2030.

* cited by examiner

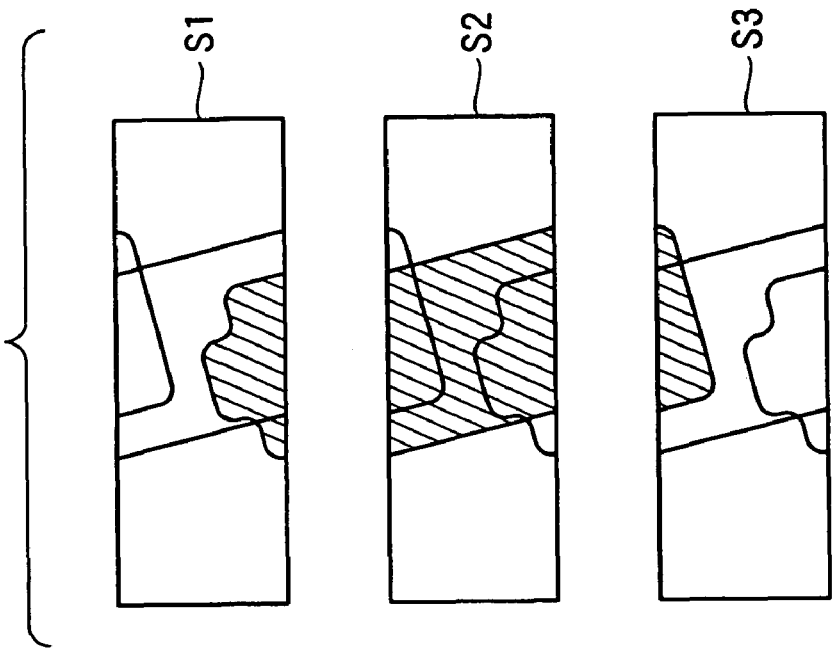
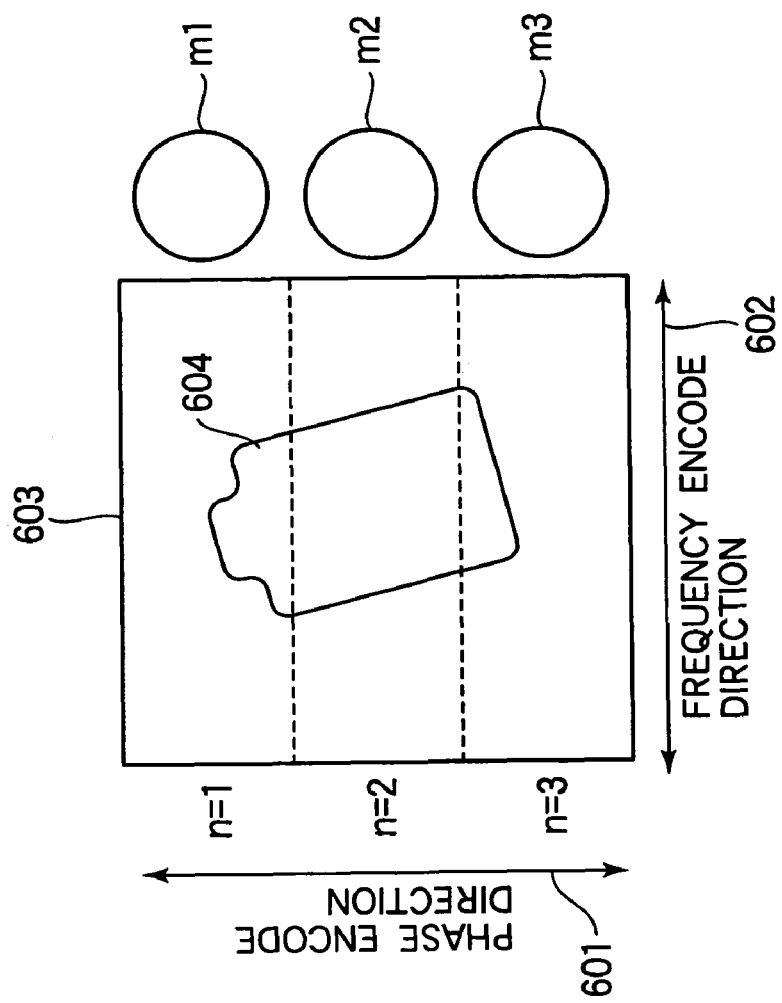

MAGNETIC RESONANCE IMAGING APPARATUS AND RF RECEPTION COIL APPARATUS

TECHNICAL FIELD

The present invention relates generally to a magnetic resonance imaging (MRI) apparatus that measures nuclear magnetic resonance (hereinafter, referred to as "NMR") signals from hydrogen, phosphorus, etc. in a patient and transforms the density distribution, the relaxation times distribution, and the like of nuclear spins into images. More particularly, the present invention relates to an MRI method and apparatus that use a plurality of RF (radio frequency) receiving coils as well as to an RF receiving coil device suitable to the MRI method and apparatus.

BACKGROUND ART

An MRI apparatus obtains echo signals necessary to reconstruction of a sheet of an image by repeatedly executing a sequence while varying an amount of phase encoding. Accordingly, an image obtaining time is greatly affected by the number of repetitions of the sequence. When high speed photographing is executed, there are ordinarily used a multi-echo type sequence, which generates a plurality of echo signals while the sequence is executed once, and a sequence whose repetition intervals are shortened to several to several tens of microseconds. However, these sequences may deteriorate an image contrast or distort an image pattern.

In contrast, a high speed photographing method called a parallel MRI method, which uses a plurality of RF receiving coils, is also proposed. In this method, the number of repetitions of the sequence is reduced by executing a measurement by thinning phase encoding steps. Ordinarily, when a measurement is executed by thinning the phase encoding steps, aliasing occurs in an image. In this method, however, the aliasing is eliminated by unfolding the aliasing portions of the image based on the sensitivity distributions of the respective RF receiving coils. As the method of eliminating the aliasing, there are known a signal processing method of executing a matrix calculation based on the sensitivity distributions of the respective RF receiving coils (SENSE: Sensitivity Encoding for Fast MRI (Klass P. Pruessmann et. al, Magnetic Resonance in Medicine 42: pp 952-962 (1999.)), and the like. That is, since images having aliasing are superimposed in the aliasing portions of the image, the aliasing of the respective images is eliminated by establishing simultaneous equations representing the correlation among the signal values (pixel values) of the images, which are reconstructed from the NMR signals of the respective RF receiving coils and have aliasing, the sensitivity distributions of the respective RF receiving coils, and the signal values (pixel values) of the images, from which aliasing is eliminated, of the respective RF receiving coils, and by solving the simultaneous equations by a matrix calculation. In principle, the number of phase encoding as many as the number of the coils used can be thinned by the matrix calculation, thereby a photographing time can be shortened.

A technology disclosed in Japanese Unexamined Patent Application Publication No. 2001-161657 is known as prior art of the parallel MRI method described above. This prior art employs a multiple array type receiving coil comprises two receiving coils which have detection sensitivity regions partitioned from each other and are juxtaposed in a plane in a partly and spatially overlapping state.

However, the receiving coils disclosed in the prior art are disadvantageous in that a merit of the MRI apparatus that a cross-sectional image can be obtained in any arbitrary direction cannot be sufficiently utilized. This is because the sensitivity regions of the coils are narrow in the depth direction with respect to a coil disposing plane and further a large field of view cannot be set in a direction orthogonal to a coil disposing direction. That is, in the receiving coil, it is restricted to arbitrarily set a phase encoding direction or a read out direction corresponding to a field of view. In particular, there is not yet proposed multiple RF receiving coils which are used in a vertical magnetic field MRI apparatus and can set a phase encoding in an arbitrary direction.

Further, multiple array type receiving coils are disclosed in "Array Head Coil for Improved Functional MRI" (Christoph Leaussler), 1996 ISMRM abstract p. 249 as well as "Helmet and Cylindrical Shaped CP Array Coils for Brain Imaging: A Comparison of Signal-to-Noise Characteristics" (H. A. Stark, E. M. Haacke), 1996 ISMRM abstract p. 1412, "8-element QD domed head array coil using inductive decoupler" (Tetsuhiko Takahashi, et al), 1998 ISMRM abstract p. 2028, "Head-neck quadrature multiple RF coil for vertical magnetic field MRI (Tetsuhiko Takahashi, Yoshikuni Matsunaga), 1997 ISMRM abstract p. 1521, "Multiple RF coils ni yoru toukeibu MRI no kousiya koukando ka (Increase in Field of View and Sensitivity of Head-Neck MRI by Multiple RF Coils))" (TAKAHASHI Tetsuo, NAGAMATSU Yoshikuni), Medical Imaging. Technology, vol 15, no. 6, pp. 734 - 741 (1997), "Four Channel Wrap-around Coil with Inductive Decouple RF or 1.5T Body Imaging" (T. Takahashi et al), 1995 ISMRM abstract p. 1418, and "MRI you koukando wrap-around RF coil-induction decoupler no multiple RF coils eno tekiyou (Application of High Sensitivity Wrap-around RF Coil-Induction Decoupler for MRI to Multiple RF Coils)", Journal of The Institute of Electronics, Information, and Communication Engineers, Vol. J80-D-II, no. 7, pp. 1964-1971 (1997).

Heretofore, various types of multiple RF receiving coils are proposed and used practically as described above. However, they are coils that are disposed optimally mainly to synthesize phased arrays and are not always optimized for the parallel MRI method. That is, when known multiple RF receiving coils are applied to the parallel MRI method, an error of a matrix calculation for eliminating aliasing may be increased depending on circumstances. Thus, an image having excellent quality may not be obtained in a short time because the aliasing eliminating arithmetic operation is not stably executed.

However, as a parallel MRI method, which can execute photographing in a wide field of view at a high speed becomes commercially practical, an apparatus, which can reconstruct an image of an arbitrary cross-section by the parallel MRI method, is desired.

Accordingly, an object of the present invention is to provide a magnetic resonance imaging method and apparatus that can obtain an image having excellent quality in a short time in the parallel MRI method.

Further, another object of the present invention is to provide a magnetic resonance imaging method and apparatus capable of improving the arbitrarily-setting property of a phase encoding direction, in addition to the above object.

In particular, an object of the present invention is to provide an RF receiving coil device for the parallel MRI method that is suitable for vertical magnetic field MRI.

DISCLOSURE OF THE INVENTION

In order to achieve the above object, the inventors made a diligent study as to the disposition of RF receiving coils and the sensitivity distributions of the respective coils suitable for a parallel MRI measurement. As a result, the inventors have achieved the present invention by finding that when a plurality of RF receiving coils each having a greatly different sensitivity distribution or sensitivity region are disposed in a phase encoding direction, an aliasing eliminating arithmetic operation can be stably executed in a parallel MRI method and an image having high quality can be obtained at a high speed.

That is, a magnetic resonance imaging method of the present invention is characterized by comprising the steps of setting an RF receiving coil, which comprises at least three RF receiving coils disposed in each of at least two orthogonal directions and have predetermined sensitivity distributions in the respective directions, to a patient, setting any one direction of the two directions as a phase encoding direction as well as measuring the magnetic resonance signals generated from the patient by executing a pulse sequence while thinning phase encoding steps, obtaining an MR image without the aliasing of the image by executing an arithmetic operation based on the magnetic resonance signals measured by at least the three RF receiving coils disposed in the set phase encoding direction and based on the sensitivity distributions of the respective RF receiving coils in the phase encoding direction thereof, and displaying the thus obtained MR image.

In this case, it is preferable that at least the three coils comprise a main RF receiving coil disposed to a diagnosing portion of the patient and at least two auxiliary RF receiving coils disposed in confrontation with each other across the diagnosing portion and that the sensitivity regions of the auxiliary RF receiving coils be narrower than that of the main RF receiving coil.

Here, the sensitivity region of the RF receiving coil means the expanse of the region the coil having a given sensitivity level in the axial direction thereof and is also referred to as the field of view of the RF receiving coil. Accordingly, when the sensitivity regions of the RF receiving coils positioned on both the sides are made narrower than that of the RF receiving coil disposed at the center, the sensitivity regions, that is, the fields of view of these RF receiving coils are greatly displaced from each other in the phase encoding direction. In other words, the sensitivity regions or the sensitivity distributions of the three RF receiving coils discretely disposed in the phase encoding direction are greatly different from each other. As a result, in the aliasing eliminating arithmetic operation executed based on the sensitivity distributions of these three RF receiving coils, since the sensitivities of the respective RF receiving coils corresponding to pixel values are greatly different, an error is unlikely to occur in the matrix calculation, thereby the aliasing eliminating arithmetic operation can be stably and securely executed.

Incidentally, it is known that the sensitivity region of the RF receiving coil in its axial direction is approximately the same as the diameter of the coil. Accordingly, when the diameter of the RF receiving coils positioned on both the sides is made smaller than that of the RF receiving coil positioned at the center, it is possible to provide the three RF receiving coils with greatly different sensitivity regions.

Further, it is preferable that the RF receiving coils positioned on both the sides and the RF receiving coil positioned at the center be disposed such that the sensitivity regions of the former RF receiving coils overlap the sensitivity region of the latter RF receiving coils at least at the edges thereof.

Another magnetic resonance imaging method of the present invention is characterized by comprising the steps of setting an RF receiving coil, which has predetermined sensitivity distributions and comprises a main RF receiving coil having a high sensitivity region of a first size and auxiliary RF receiving coils each having a high sensitivity region of a second size smaller than that of the main RF receiving coil and disposed across the main RF receiving coil, to a patient, measuring the magnetic resonance signals from a diagnosing portion of the patient by applying gradient magnetic fields and high frequency magnetic fields to the patient while thinning phase encoding steps, obtaining an MR image without the aliasing of the image by executing an arithmetic operation based on the magnetic resonance signals received by the RF receiving coil and based on the sensitivity distributions of the RF receiving coil, and displaying the thus obtained MR image.

According to the above magnetic resonance imaging method, it is possible to obtain a uniform image having high quality by the main RF receiving coil having the relatively large sensitivity region, that is, having the relatively large field of view, thereby an image excellent in uniformity can be obtained.

In this case, it is preferable that the respective auxiliary RF receiving coils and the main RF receiving coil be disposed such that the sensitivity regions of the former coils overlap the sensitivity region of the latter coil at least at the edges thereof. Further, the step of obtaining the MR image without the aliasing of the image may comprise a step of executing the matrix calculation of simultaneous equations obtained based on the correlation among the magnetic resonance signals measured by the main RF receiving coil and the respective auxiliary RF receiving coils, the sensitivity distributions of the main and auxiliary RF receiving coils, and the MR image data without the aliasing of the image.

Further, when two or three sets of auxiliary RF receiving coils each set including at least two auxiliary RF receiving coils are disposed in two or three orthogonal directions, respectively across a diagnosing portion, the aliasing of a cross-sectional image can be eliminated based on the NMR signals received by the main RF receiving coil and the one set of the respective RF receiving coils disposed in confrontation with each other in the phase encoding direction and based on the sensitivity distributions of the respective RF receiving coils. That is, since the two or three sets of the auxiliary RF receiving coil groups are disposed so as to detect the magnetic fields of the two or three axes that are orthogonal to each other, the arbitrarily-setting property of the phase encoding direction can be improved by selecting one set of the auxiliary RF receiving coil group disposed in the phase encoding direction from the two or three sets of the RF receiving coil groups. In particular, when the three sets of the auxiliary RF receiving coil groups are applied, the parallel MRI measurement can be executed using an arbitrary direction as the phase encoding direction and moreover an image having high uniformity can be obtained. Further, the aliasing of the image occurring in the direction can be securely eliminated. With the above arrangement, any arbitrary cross-sectional image can be photographed at a high speed.

In contrast, a magnetic resonance imaging apparatus of the present invention is characterized by comprising a magnetic field generation means for applying gradient magnetic fields and high frequency magnetic fields to a patient placed in static magnetic fields in a predetermined pulse sequence while thinning phase encoding steps, a receiving coil group comprising a plurality of RF receiving coils for receiving the nuclear magnetic resonance signals generated from the patient, and an image reconstruction means for reconstructing an image by processing the nuclear magnetic resonance signals, wherein the receiving coil group comprises at least three RF receiving coils disposed in each of at least two orthogonal directions, and any one of the two directions is set as a phase encoding direction, and the image reconstruction means comprises a means for eliminating the aliasing of the image by an arithmetic operation executed using the magnetic resonance signals received by at least the three RF receiving coils, which are disposed in the phase encoding direction, of the RF receiving coils and using the sensitivity distributions of these RF receiving coils.

Further, in place of the above receiving coil groups, it is possible to apply receiving coil groups which include at least one main RF receiving coil and two or three sets of auxiliary RF receiving coils each set including at least two auxiliary RF receiving coils, wherein the main RF receiving coil has a high sensitivity region in a diagnosing portion of a patient, and each set of the auxiliary RF receiving coils are disposed in confrontation with each other across the diagnosing portion in two or three orthogonal directions and have a high sensitivity region formed narrower than that of the main RF receiving coil. In this case, the image reconstruction means reconstructs an image from which aliasing is eliminated by an arithmetic operation executed based on the magnetic resonance signals received by the main RF receiving coil and the one set of the RF receiving coils disposed in confrontation with each other at least in the phase encoding direction and based on the sensitivity distributions of these coils.

Further, an orthogonal detection coil (QD coil) can be applied as the main RF receiving coil.

On the other hand, a receiving coil device of the present invention can be realized by at least one main RF receiving coil having a sensitivity region whose size can cover an overall diagnosing portion and a plurality of auxiliary RF receiving coils each having a sensitivity region narrower than that of the main RF receiving coil, wherein the auxiliary RF receiving coils are divided into three sets of auxiliary RF receiving coil groups, the auxiliary RF receiving coils included in each group can be disposed in confrontation with each other at a position across the main RF receiving coil, and the auxiliary RF receiving coil groups including the respective sets of the auxiliary RF receiving coils can be disposed in three directions that are orthogonal to each other.

In this case, the QD coil having a relatively large field of view covering approximately the overall diagnosing portion can be used as the main RF receiving coil. As described above, it is possible to obtain an image having high quality in various types of MRI methods including the parallel MRI method by combining the RF receiving coils each having a different object.

BRIEF DESCRIPTION OF THE DRAWINGS

FIGS. 6(A) and 6(B) are views explaining a parallel MRI method in the present invention.

BEST MODE FOR CARRYING OUT THE INVENTION

An MRI apparatus to which a magnetic resonance imaging method of the present invention is applied will be described below in detail with reference to the drawings.

Figure 1:
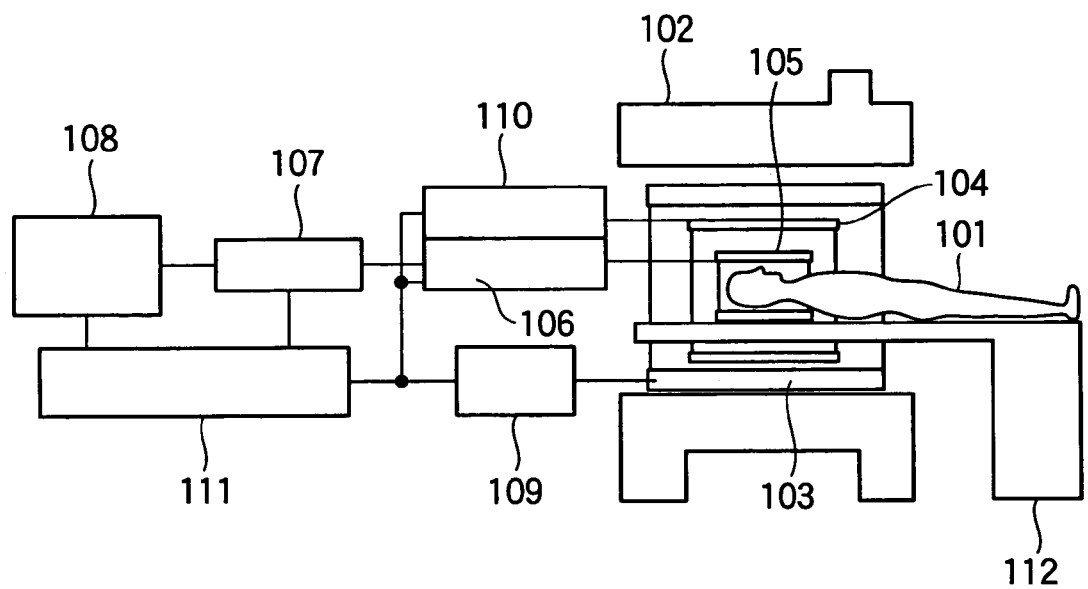
FIG. 1 is a view showing the overall arrangement of an MRI apparatus to which the present invention is applied.

FIG. 1 shows the arrangement of a typical MRI apparatus. The MRI apparatus includes a magnet 102 for generating a vertical static magnetic field in the space of a periphery including a patient 101, a gradient magnetic field coil 103 for generating gradient magnetic fields in the space, an RF coil 104 for generating a high frequency magnetic field in the region, and an RF probe 105 acting as an RF receiving coil device for detecting the NMR signals generated by the patient 101 and further includes a bed 112 on which the patient 101 lies.

The gradient magnetic field coil 103 comprises gradient magnetic field coils in three directions or x-, y- and z-directions, and these coils generate gradient magnetic fields, respectively according to a signal from a gradient magnetic field power supply 109. A photographing cross-section can be set in any arbitrary direction depending on a manner for applying the gradient magnetic fields. The RF coil 104 generates a high frequency magnetic field having the same frequency as the resonance frequency of the nuclear spins that are a subject to be photographed. Although the subject to be photographed in the MRI apparatus is ordinarily protons that are a material mainly constituting a human body, the subject is not limited thereto.

The nuclear magnetic resonance signal, which is generated from the subject by applying the high frequency magnetic field, is detected by a signal detection unit 106 as the signal of the RF probe 105, processed by a signal processing unit 107, and further converted into an image signal by a calculation. An image is displayed on a display unit 108. The gradient magnetic filed power supply 109, an RF transmission unit 110, and the signal detection unit 106 are controlled by a controller 111. A control time chart is ordinarily called a pulse sequence, and a pulse sequence determined according to a photographing method is previously built in a memory unit of the controller 111 as a program. In the MRI apparatus of the present invention, in order to execute a parallel MRI method as a photographing method which executes a measurement by thinning the encode steps of a phase encoding at a predetermined thinning rate, the parallel MRI method can be selected through an input unit of the controller 111 in a predetermined pulse sequence as well as the thinning rate of the encode steps can be designated. A photographing sequence employing the parallel MRI method will be described alter.

Further, the MRI apparatus of the present invention uses an RF probe comprising a plurality of RF receiving coil groups each having a different object as the RF probe 105 suitable for the parallel MRI method. Specifically, the RF probe 105 comprises at least one main RF receiving coil having a large field of view for viewing approximately an overall diagnosing portion and a group of a plurality of auxiliary RF receiving coils each having a scope of view smaller than that of the main RF receiving coil and viewing a part of the diagnosing portion. In this embodiment, the group of the auxiliary RF receiving coils each having the small field of view comprise three sets of auxiliary RF receiving coils disposed in three directions that are orthogonal to each other.

Figure 2:
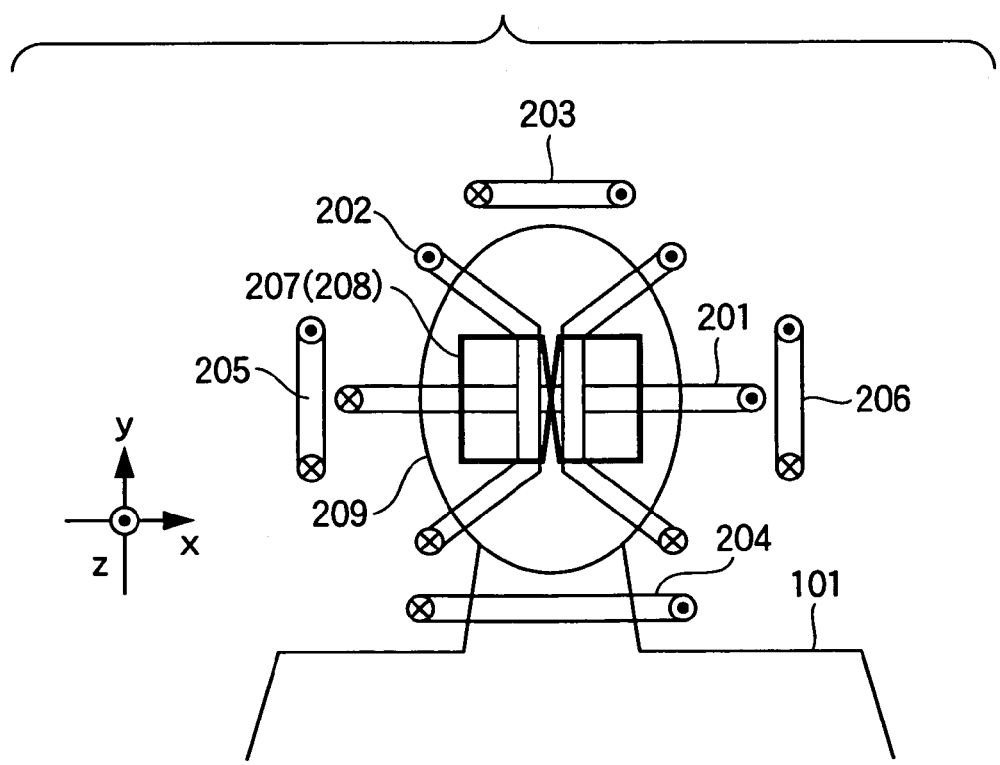
FIG. 2 is a view showing an embodiment of an RF probe of the present invention.

FIG. 2 shows an RF probe used for a head in a vertical magnetic field as an embodiment of the RF probe of the present invention. In the figure, a horizontal direction is an x-direction, an up/down direction is a y-direction, and a direction vertical to a sheet surface is a z-direction.

The RF probe includes a solenoid coil 201 for detecting a y-direction component of a rotary magnetic field and a saddle coil 202 for detecting an x-direction component thereof as the main RF receiving coil for the large field of view and includes three sets of coils 203 to 208 for detecting the components in the x-, y-, and z-directions, respectively as the auxiliary RF receiving coils for the small field of view.

The detecting region of the solenoid coil 201 overlaps the detecting region of the saddle coil 202 as well as the coils 201 and 202 have broad sensitivity characteristics and cover approximately the overall head of a patient 209. Since these coils 201 and 202 detect orthogonal high frequency magnetic fields, they also act as known QD coils by executing QD synthesization.

The coils 203 and 204 for the small field of view are coils for detecting a magnetic field projected in the y-direction likewise the coil 201 and disposed above and below the head. The diameter of these coils 203 and 204 is smaller than that of the coil 201, and thus they have a small sensible region. In the coils 203 and 204, the coil 203 positioned above the head may be any of a solenoid coil and an "8-shaped" coil, the "8-shaped" coil is preferable because it has a shallow sensitivity in the y-direction, and, in particular, an "8-shaped" coil having a long central conductor in the z-direction is preferable. The "8-shaped" coil can obtain a high sensitivity in a shallow region and can execute a stable aliasing removing arithmetic operation in the parallel MRI method that will be described later. A solenoid coil is used as the coil 204 positioned around a neck.

The coils 205 and 206 are coils for detecting the magnetic field projected in the x-direction likewise the saddle coil 202 and positioned on both the sides of the head. The diameter of the coils 205 and 206 is smaller than that of the coil 202, and thus they have a small sensible region. Any one of a solenoid coil and an "8-shaped" coil may be used as the coils 205 and 206, and when the "8-shaped" coil is used, a coil having a long central conductor in the z-direction is used preferably because it has a high sensitivity.

The coils 207 and 208 are disposed in front of a face and behind the head in parallel with an x-y plane (FIG. 2 shows only the coil 207 disposed in front of the face). These coils comprise "8-shaped" coils and detect the projecting magnetic field of the component, which is vertical (x-direction in the figure) to the center line (the direction in which the central conductor travels) of the "8-shaped" coil, of the rotary magnetic field on the x-y plane. The central conductor of the "8-shaped" coil is provided with a higher sensitive by increasing its length in the x- or y-direction. Note that although FIG. 2 shows a case that the letter "8" is arranged in a lateral direction, the direction of it may be set arbitrarily.

Induction coupling is eliminated from these coils 201 to 208. Known methods such as a low impedance method, an induction decoupler method, and the like may be employed as an induction coupling eliminating method.

Figure 3:
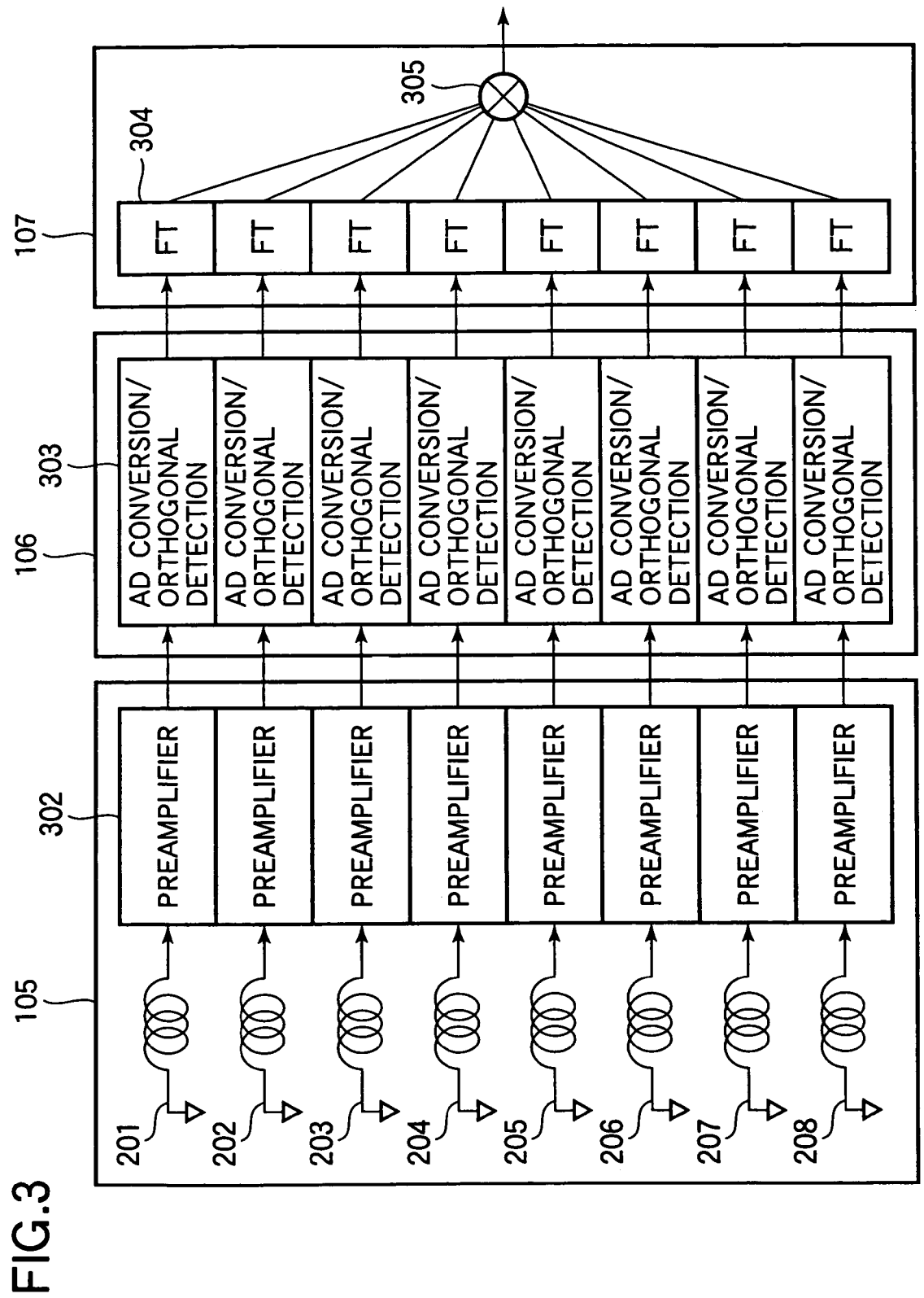
FIG. 3 is a view showing the arrangement of a receiving unit of the RF probe of the present invention.

FIG. 3 shows the arrangements of the signal detection unit 106 and the signal processing unit 107 of the MRI apparatus employing the above RF probe. The eight RF receiving coils 201 to 208 are connected to preamplifiers 302, respectively and constitute the single multiple RF receiving coil 105. The signal detection unit 106 comprises eight A/D conversion and orthogonal detection circuits 303 which are arranged in parallel with each other and to which the outputs from the respective preamplifiers 302 are connected.

The signal processing unit 107 includes an arithmetic operation means 304, which synthesizes the signals from the respective receiving coils, that is, places the signal of each coil in a measuring space (k space) and reconstructs an image by subjecting the synthesized signals to Fourier transform (FT), back projection, wavelet conversion, and the like, and a signal synthesizing means 305 for synthesizing image data. The signal synthesizing means 305 further includes a means for executing a matrix calculation for eliminating aliasing artifacts when the image is synthesized.

In the RF probe arranged as described above, since the three sets of the RF receiving coils are disposed in the three orthogonal directions, a measurement can be executed at a high speed in any arbitrary phase encoding direction in the parallel MRI-measurement described below. Further, since the sensitivity distributions of the respective RF receiving coils are greatly different in the respective phase encoding directions, the above matrix calculation can be executed stably.

Figure 4:
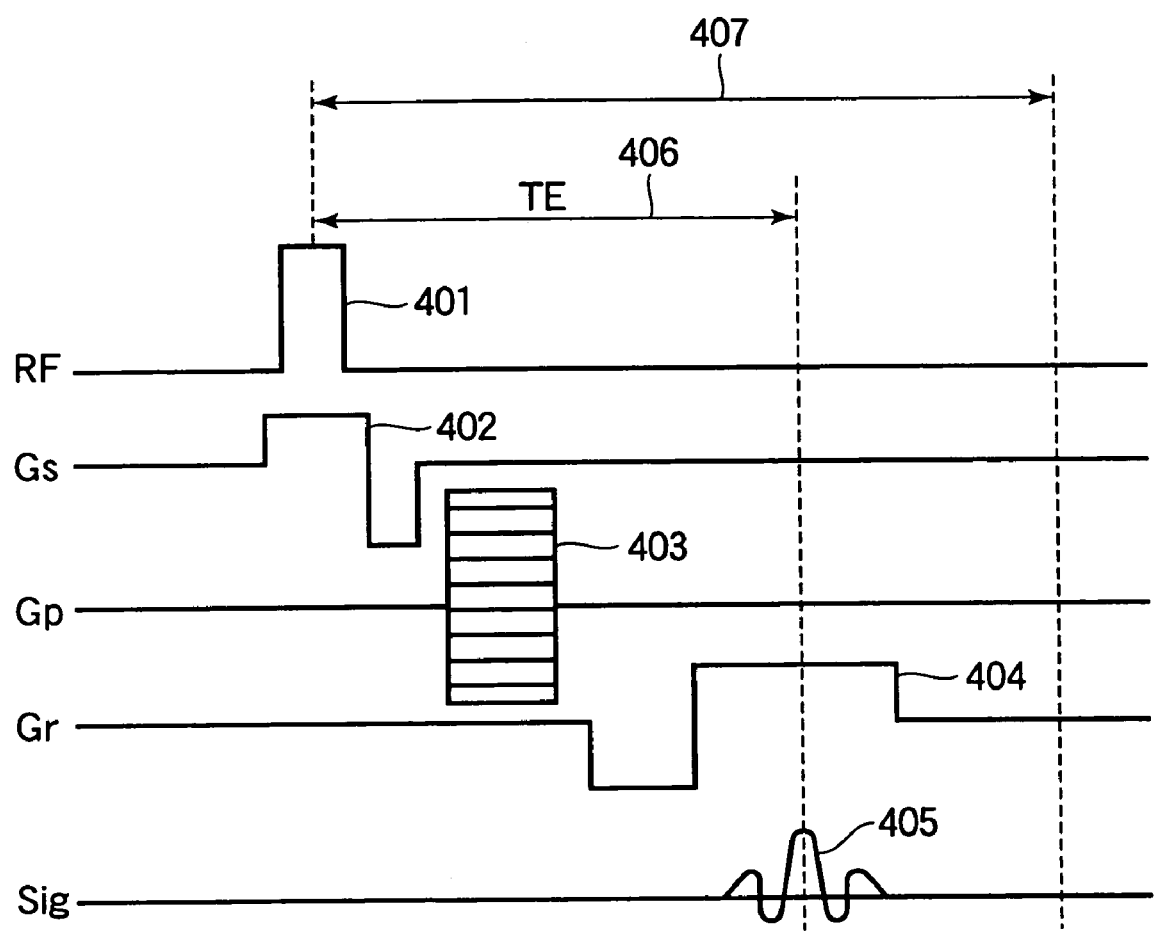
FIG. 4 is a view explaining a sequence of ordinary gradient echoes.

Next, a photographing method and a signal processing method in the MRI apparatus described above will be explained below. Although ordinary spin echo and gradient echo sequences can be employed as the photographing method, the present invention is characterized in that echo signals are measured in parallel. As an example, FIG. 4 shows the ordinary gradient echo sequence. In this pulse sequence, after a high frequency pulse 401 and a slice selection gradient magnetic field pulse 402 are applied, a phase encoding gradient magnetic field pulse 403 and a reading-out gradient magnetic field pulse 404 are applied, and an echo signal 405, which is an NMR signal, is measured after a predetermined time (echo time) passes from the time at which the high frequency pulse 401 was applied. The echo signal 405 is ordinarily obtained as a time series signal comprise 128, 256, 512, or 1024 pieces of sampling data. This sequence is repeated during a repetition time 407. At the time, a set of echo signals (measured data) as many as the phase encodings necessary to reconstruct an image is obtained by changing the intensity of the phase echo gradient magnetic field 403 each time the sequence is repeated. Ordinarily, a value 64, 128, 256, 512, or the like is selected as the number of the phase encodings in consideration of a field of view and a spatial resolution. An MR image is created by subjecting the data to two-dimensional Fourier transform.

Figure 5A:
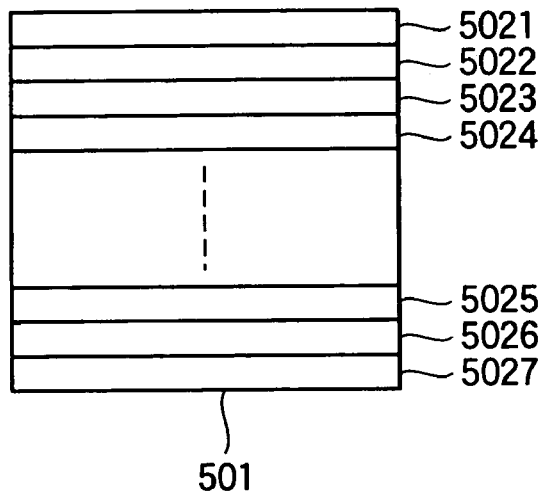
FIGS. 5(A) to 5(D) are views explaining a measurement executed by a parallel MRI.
Figure 5B:
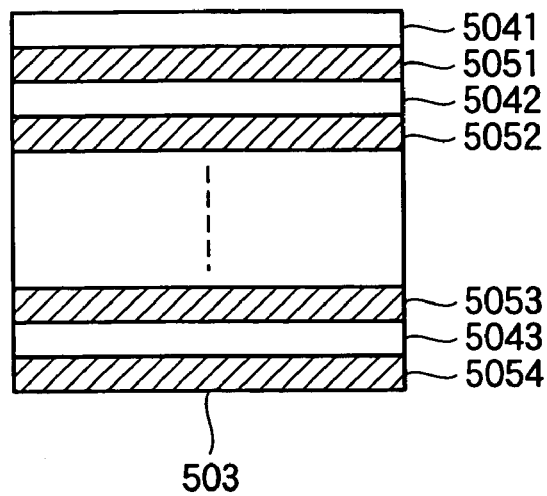
Figure 5C:
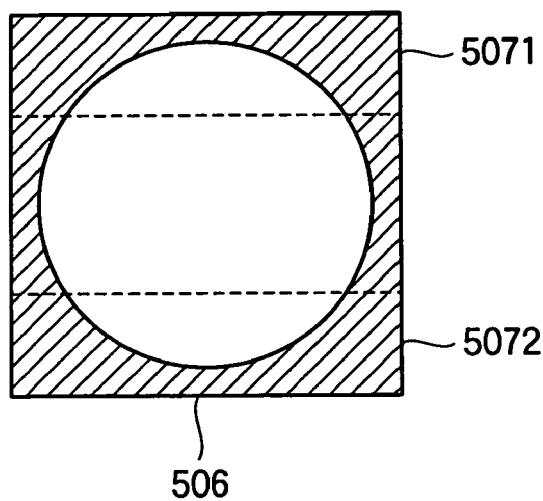
Figure 5D:
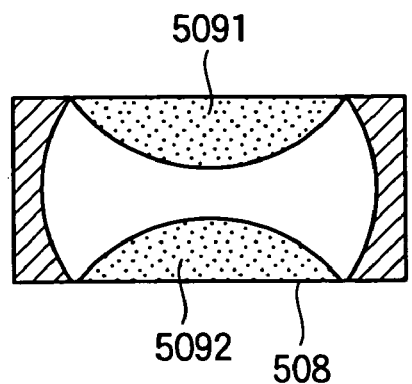

In the parallel MRI measurement, photographing is executed by thinning the phase encoding steps at an appropriate thinning rate in the repetition of the pulse sequence. As shown in, for example, FIG. 5, the data 501 (5021 to 5027) of all the lines that occupy the k space is measured in ordinary photographing (FIG. 5(A)), whereas, in the parallel photographing, data of every other line is measured as shown in FIG. 5(B). In FIG. 5(B), reference numerals 504 (5041 to 5043) shows data to be measured, and data 505 (5051 to 5054) shows data not to be measured. In this case, since the number of data to be measured is half the data that is measured ordinarily, a photographing speed is reduced to half. However, when an image is created by reducing the number of matrixes to half, an image 508 in which aliasing is produced is obtained as shown in FIG. 5(D). The aliasing portions 5091 and 5092 correspond to the upper portion 5071 and the lower portion 5072 of an ordinary image 506 (FIG. 5(C)). In the parallel measurement, the image 506 as shown in FIG. 5(C) is obtained by eliminating the aliasing, that is, by unfolding the aliasing portions by subjecting the data obtained from the respective RF receiving coils to an arithmetic operation.

Next, the aliasing eliminating arithmetic operation will be explained. The aliasing eliminating arithmetic operation and a signal synthesization are executed as to a plurality of RF receiving coils, which have a different sensitivity distribution in the phase encoding direction, among the recording head coils 201 to 208 that constitute the RF receiving coil group shown in FIG. 2. In the aliasing eliminating arithmetic operation, image data (magnetized distribution) from which the aliasing is eliminated is: obtained by previously determining the sensitivity distributions of the respective RF receiving coils as reference data and unfolding the image data obtained by the measurement executed by thinning the phase encoding steps. Since the sensitivity distributions can be also determined by processing the data in the low frequency region of the k space by a low-pass filter, the data in the low frequency region may be previously measured as the reference data, or the data, which is in the low frequency region of the k space, of the measured data, may be used as the reference data. Otherwise, the data in the low frequency region of finally measured data may be used as the reference data. An example of the arithmetic operation when three coils each having the small field of view are used will be shown below.

As shown in FIG. 6(A), it is assumed that three coils m1 to m3 are disposed which have a different sensitivity distribution in a phase encoding direction 601 with respect to an FOV 603 that is prescribed by the phase encoding direction 601 and a frequency encode direction 602. When it is assumed, for example, that the coils m1 to m3 correspond to the coils shown in FIG. 2, they correspond to the set of the coils 205, 202, and 206, the set of the coils 203, 201, and 204, and the set of the coils 207, 201 (or 202) and 208, respectively. However, in the example of FIG. 3, a coil having a small field of view is used as the coil m2 in place of the coils 201 and 202 with the large field of view shown in FIG. 2. Signals S1 to S3 (FIG. 6(B)), which have the signal intensity distributions according to the sensitivity distributions of the respective coils m1 to m3, can be obtained from the coils. In the illustrated example, a phantom 604 is photographed as a subject. The signal value Sm (m shows No. of coil, and m in the subsequent description also shows No. of coil) of the phantom 604 can be represented by the following equation when the sensitivity distribution is shown by Am, n (n shows No. of field of view, and n in the subsequent description also shows No. of field of view) and the magnetization distribution in each field of view is shown by Pn.

$$\begin{pmatrix} S1 \\ S2 \\ S3 \end{pmatrix} = \begin{pmatrix} A1,1 & A1,2 & A1,3 \\ A2,1 & A2,2 & A2,3 \\ A3,1 & A3,2 & A3,3 \end{pmatrix} \cdot \begin{pmatrix} P1 \\ P2 \\ P3 \end{pmatrix}$$ [Equation 1]

Accordingly, a magnetization distribution P as to an overall field of view can be determined by the following equation 2 by expanding the above determinant.

$$S = A \cdot P$$ [Equation 2]

Accordingly, $P = A^{-1} \cdot S$ (here, $A^{-1}$ represents inverse matrix)

Image data, from which the aliasing included in the measured data is eliminated, can be obtained by the matrix calculation. In the embodiment of FIG. 2 in which the three sets of the coils (x-direction: 205, 202 (or 201), 206, y-direction: 203, 201, (or 202), 204, z-direction: 207, 201, (or 202), 208) are disposed in the three orthogonal directions, when the matrix calculation described above is executed as to the three coils arranged in the phase encoding direction, synthesized image data, from which the aliasing of the two or three sets corresponding to the respective coils is eliminated, can be obtained (at a double or triple speed). Further, since the coils 201 and 202, which have the large field of view, of the three sets of the coils are disposed at the center in the MRI apparatus of the above embodiment, there can be obtained an effect of mainly eliminating the aliasing by the local data of the two sets of the coils and improving the S/N of the synthesized image by the data from the coils 201 and 202 that have the large field of view and have been subjected to the QD synthesization.

As described above, according to the embodiment described above, the parallel MRI method is characterized in that, as the plurality of RF receiving coils, the three RF receiving coils (for example, coils 205, 202, 206) are discretely disposed in confrontation with each other about the diagnosing portion in the phase encoding direction, and coils, which have a sensitivity region narrower than that of the RF receiving coil (for example, coil 202) disposed at the center, are selected as the RF receiving coils (for example, coils 205, 206) positioned on both the sides of the above coils. With this arrangement, the distributions of sensitivities of the three discretely disposed RF receiving coils are greatly different from each other. Accordingly, since the sensitivities of the respective RF receiving coils corresponding to the signal values are greatly different in the aliasing eliminating arithmetic operation executed based on the distributions of sensitivities of the three RF receiving coils, the matrix calculation is unlike to diverge, for example, a result, which is obtained from the processing for dividing a certain value by zero or a value infinitely near to zero, is unlike to diverge, thereby the aliasing eliminating arithmetic operation can be stably and securely executed.

Note that it is preferable that the RF receiving coils on both the sides and the RF receiving coils at the center be disposed such that the sensitivity regions of the former coils overlap the sensitivity regions of the latter coils at least at the edges thereof.

In particular, the embodiment is characterized in that the coils 201 or 202, which is the main RF receiving coil and has the sensitivity region whose size corresponds to the diagnosing portion of the patient 209, is disposed at the diagnosing portion and that the coils 203 and 204, the coils 205 and 206, and the coils 207 and 208, which are the three sets of the auxiliary RF receiving coils and have the sensitivity region narrower than that of the coil 201 or 202, are discretely disposed in confrontation with each other across the diagnosing portion in a desired phase encoding direction. That is, the fields of view of at least the three coils disposed in the same direction do not entirely overlap with each other. Accordingly, the aliasing elimination arithmetic operation described above can be stably executed. Further, a uniform image having high quality can be obtained by the coil 201 or 202 that is the main RF receiving coil having the relatively large field of view, thereby an image excellent in uniformity can be obtained. In contrast, the aliasing can be eliminated by the coils 203 and 204, the coils 205 and 206, and the coils 207 and 208 that are the auxiliary RF receiving coils. As described above, the embodiment is characterized in that the receiving coil group is arranged such that the object of each coil included in the coil group is made distinct.

Further, according to the embodiment, the coils of the three sets of the coils 203 and 204, the coils 205 and 206, and the coils 207 and 208, which are the auxiliary RF receiving coils, are disposed in the three orthogonal directions, respectively in confrontation with each other across the diagnosing portion so as to detect the magnetic fields of two or three orthogonal axes, thereby the arbitrarily-setting property of the phase encoding direction can be improved. In particular, when the three sets of the coils are applied, the parallel MRI measurement can be executed by setting an arbitrary direction as the phase encoding direction, and moreover an image excellent in uniformity can be obtained. Further, the aliasing of the image occurring in the phase encoding direction can be securely eliminated, thereby any arbitrary cross-sectional image can be photographed at a high speed.

Further, when, for example, the phase encoding direction is set in the y-direction, although the coils having the same sensitivity region in the y-direction may be subjected to the above matrix calculation, they may be subjected to the ordinary synthesization (weighted synthesization) of multiple array coils. For example, the coils 205, 202, 201, 207, 208, and 206 may be subjected to the weighed synthesization because the sensible portions of the coils are not dispersed in the y-direction, and the above matrix calculation may be executed as to three images, that is, the image resulting from the above synthesization and the images obtained by the coils 203 and 204. This idea can be also applied to the x- and y-directions likewise.

According to this embodiment, since the three sets of the six coils 203 to 208 are disposed around the patient in the three directions, a set of a plurality of coils, which are disposed in an arbitrary phase encoding direction (any of the x-, y- and z-directions), can be selected, thereby the photographing speed in the parallel MRI apparatus can be increased. That is, when three coils are selected, a photographing speed can be triplicated at the maximum. It is needless to say that the coils (signals) used to eliminate aliasing are not limited to three coils, and it is possible to more increase the photographing speed by employing a larger number of coils. Further, according to the embodiment, since the sensitivity characteristics of the respective RF receiving coils are greatly different from each other, the matrix calculation can be stably executed in the parallel MRI apparatus, thereby a stable image whose quality is not deteriorated by signal processing can be obtained.

Further, according to the embodiment, since the signals from the coils having the small field of view (coils 203 and 204, the coils 205 and 206, and the coils 207 and 208) are synthesized with the signals from the coils having the large field of view (coils 201 or/and 202), an image having a high degree of uniformity can be obtained in its entirety.

The MRI apparatus of the present invention has been explained with reference to the embodiment shown in FIG. 2. In the embodiment, the case that aliasing is eliminated by synthesizing the three coils, each of which has a different sensitivity distribution in the phase encoding direction, of the three sets of the RF receiving coils, has been explained. However, any arbitrary combination of the coils can be selected according to the phase encoding direction. In the above explanation the case, for example, that aliasing eliminating/synthesizing processing is executed to the signals from the coils having the small field of view has been explained. However, the signals from the coils having the large field of view may be subjected to the arithmetic operation for the aliasing elimination/synthesization in place of being subjected to the QD synthesization.

Further, the embodiment has explained the MRI apparatus including the RF probe in which the three sets of the coils that have the small field of view are combined with the one set of the coil that has the large field of view and can be subjected to the QD synthesization. However, the present invention is not limited to the above embodiment and can be variously modified.

Figure 7C:
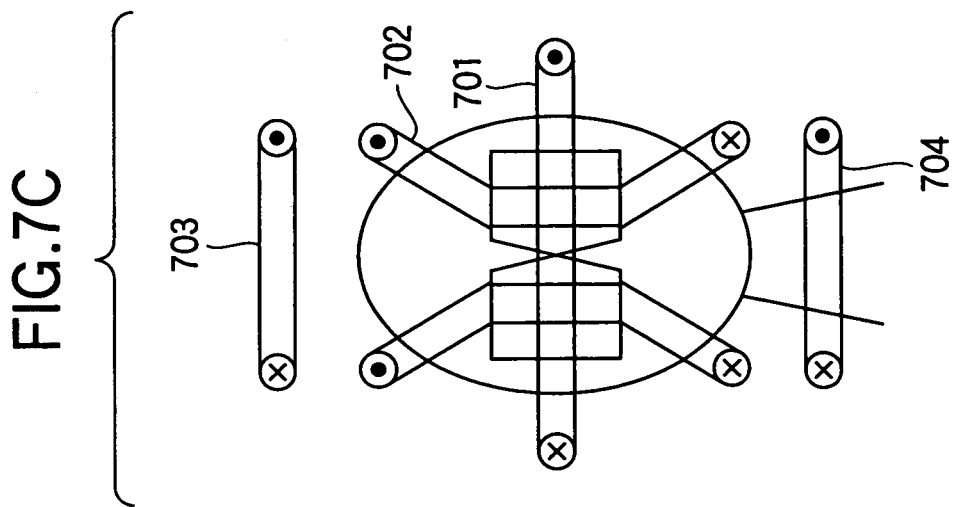
FIGS. 7(A) to 7(C) are views showing other embodiments of the RF probe of the present invention.
Figure 7B:
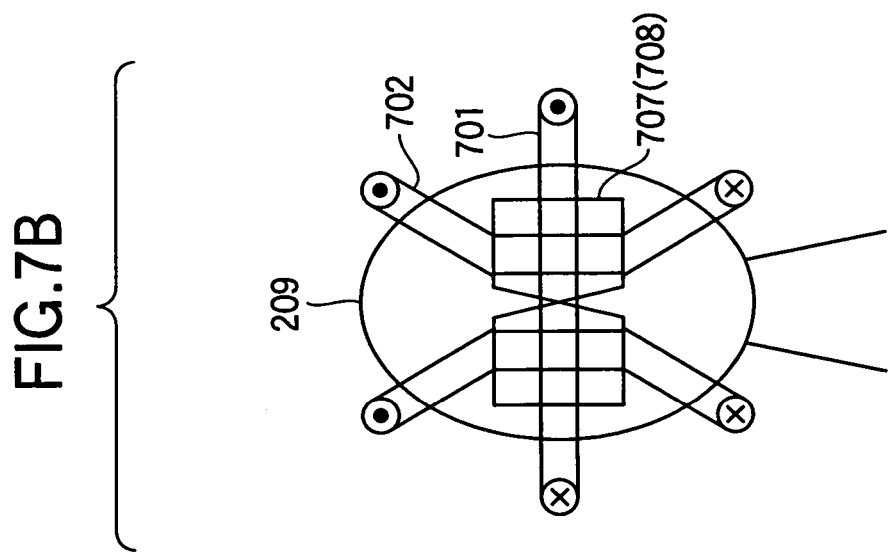
Figure 7A:
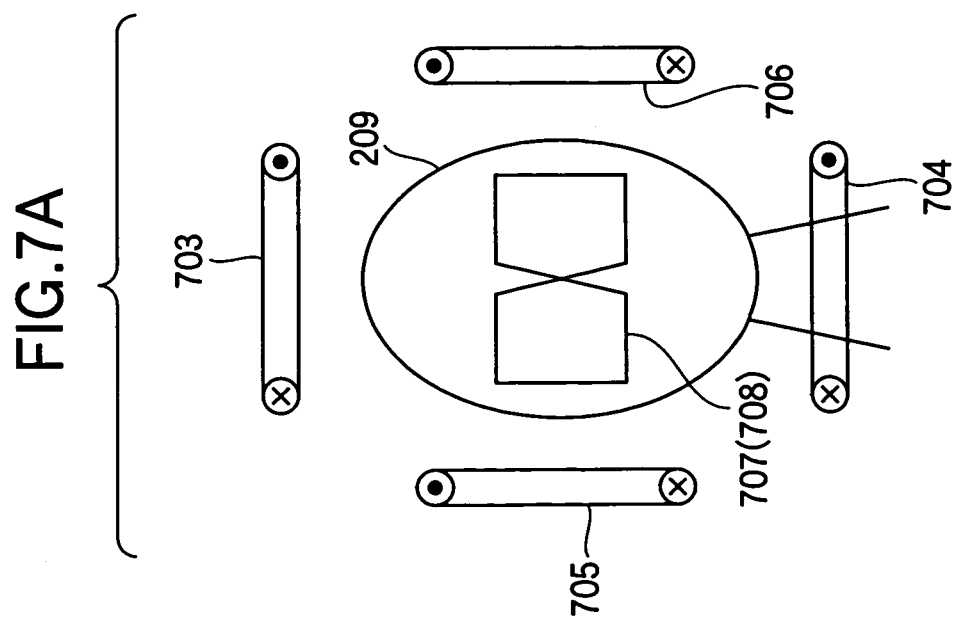

For example, as shown in FIG. 7(A), the RF probe may comprises three sets of coils 705 and 706, coils 703 and 704, and coils 707 and 708 each having a small field of view omitting a coil having a large field of view. Otherwise, as shown in FIGS. 7(B) and 7(C), the RF probe may comprises coils 701 and 702 having a large field of view and one or two sets of coils 707 and 708 and coils 703 and 704 each having a small field of view. In this case, a degree of freedom, which can be obtained when the coils are disposed in the three directions, cannot be obtained in the parallel MRI measurement. However, when at least one set of the coils are disposed in a direction which is used as the phase encoding direction where signals are often measured, this arrangement can be applied to the parallel MRI measurement, thereby it is possible to execute a stable matrix calculation by the difference between the sensitivity distributions of the coils similarly to the case that the coils are disposed in the three directions.

Figure 8:
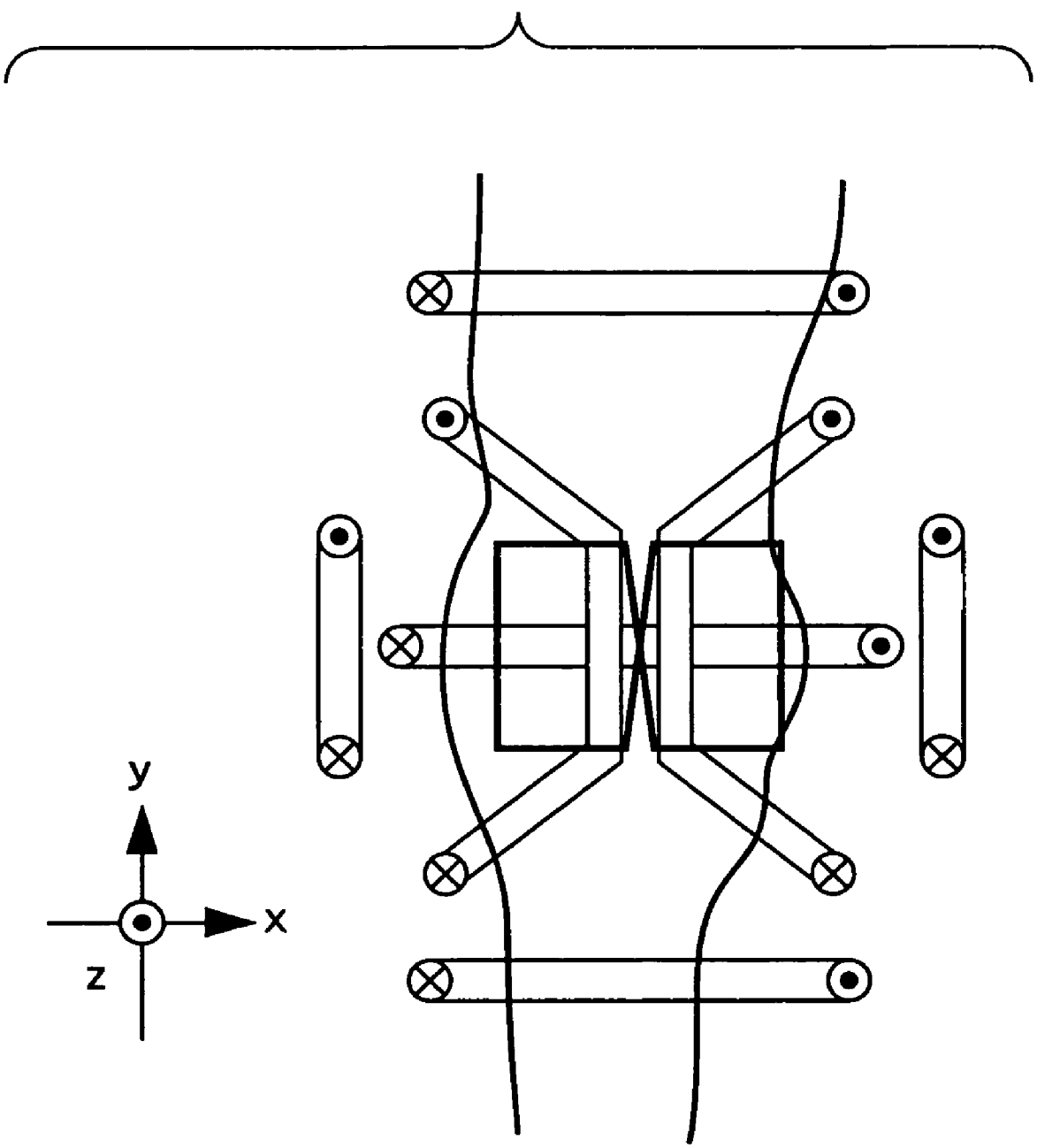
FIG. 8 is a view showing still other embodiment of the RF probe of the present invention.

Further, although the above embodiment shows the RF probe used for the head, RF probe used to other portions such as a knee, a belly, and the like can be arranged similarly. FIG. 8 shows an RF probe for a knee used in a vertical magnetic field. The explanation of the shapes of the coils used in this RF probe is omitted because they are the same as those of the coils shown in FIG. 2. A photographing speed can be, for example, triplicated also in an MRI apparatus using this RF probe by executing the parallel MRI measurement. On the contrary, however, a triple-high spatial resolution can be obtained in a photographing time as long as an ordinary photographing time. an image having a 256×768 spatial resolution can be obtained in a photographing time of, for example, 256×256 matrices, which is very advantageous when a portion such as a knee having a complex structure is photographed.

Further, the present invention can be also applied to a three-dimensional measurement. In this case, the photographing speed may be increased by thinning the data not only in the phase encoding direction but also the data in a slice encode direction whose concept is the same as that of the phase encoding direction, or by thinning the data by combining the phase encoding direction and the slide direction.

As described above according to the present invention, an image having excellent quality can be obtained in the parallel MRI method.

Further, when two or three sets of the auxiliary RF receiving coil groups are disposed in confrontation with each other in the two or three orthogonal directions, the arbitrarily-setting property of the phase encoding direction can be improved.

In particular, the RF receiving coil groups suitable for the MRI method using the vertical magnetic field can be realized.

The invention claimed is:

1. A magnetic resonance imaging apparatus comprising:
   magnetic field generation means for applying gradient magnetic fields and high frequency magnetic fields to a patient placed in static magnetic fields in a predetermined pulse sequence while thinning phase encoding steps, a receiving coil group comprising a plurality of RF receiving coils for receiving the nuclear magnetic resonance signals generated from the patient, and image reconstruction means for reconstructing an image by processing the nuclear magnetic resonance signals, wherein
   the receiving coil group comprises at least one main RF receiving coil having a high sensitivity region in a diagnosing portion of the patient and at least two sets of auxiliary RF receiving coil groups each set including at least two auxiliary RF receiving coils disposed in confrontation with each other in either of at least two orthogonal directions, and the high sensitivity region of the respective auxiliary RF receiving coils is formed narrower than that of the main RF receiving coil; and the image reconstruction means eliminates the aliasing of an image by an arithmetic operation executed based on the magnetic resonance signals received by the main RF receiving coil and at least one set of the respective auxiliary RF receiving coils disposed in confrontation with each other in at least a phase encoding direction and based on the sensitivity distributions of these RF receiving coils.

2. A magnetic resonance imaging apparatus according to claim 1, characterized in that three sets of the auxiliary RF receiving coil groups are disposed in three orthogonal directions.

3. A magnetic resonance imaging apparatus according to claim 1, characterized in that at least one of the RF receiving coils is a solenoid coil.

4. A magnetic resonance imagine apparatus according to claim 1, characterized in that at least one of the RF receiving coils is a saddle coil.

5. A magnetic resonance imaging apparatus according to claim 1, characterized in that at least one of the auxiliary RF receiving coils is a solenoid coil.

6. A magnetic resonance imaging apparatus according to claim 1, characterized in that at least one of the auxiliary RF receiving coils is a 8-shaped coil.

7. A magnetic resonance imaging apparatus comprising:

magnetic field generation means for applying gradient magnetic fields and high frequency magnetic fields to a patient placed in static magnetic fields in a predetermined pulse sequence while thinning phase encoding steps, a receiving coil group comprising a plurality of RE receiving coils for receiving the nuclear magnetic resonance signals generated from the patient, and image reconstruction means for reconstructing an image by processing the nuclear magnetic resonance signals, wherein the receiving coil group comprises at least three RF receiving coils disposed in each of at least two orthogonal directions, and any one of the two directions is set as a phase encoding direction; and the image reconstruction means comprises means for eliminating the aliasing of the image by an arithmetic operation executed using the magnetic resonance signals received by at least the three RF receiving coils, which are disposed in the phase encoding direction, of the RF receiving coils and using the sensitivity distributions of these RF receiving coils.

8. A magnetic resonance imaging apparatus according to claim 7, characterized in that at least the three coils comprise a main RF receiving coil disposed to a diagnosing portion of the patient and at least two auxiliary RF receiving coils disposed in confrontation with each other across the diagnosing portion, and the sensitivity regions of the auxiliary RF receiving coils are narrower than that of the main RF receiving coil.

9. A magnetic resonance imaging apparatus according to any one of claims 1, 2, and 8, characterized in that the respective auxiliary RF receiving coils and the main RF receiving coil are disposed such that the sensitivity regions of the respective auxiliary RF receiving coils overlap the sensitivity region of the main RF receiving coil at least at the edges thereof.

10. A magnetic resonance imaging apparatus according to any one of claims 1, 2, 7, and 8, characterized in that the main RF receiving coil is an orthogonal direction coil.

* * * * *